(12) United States Patent
Hacker et al.

(10) Patent No.: US 9,044,694 B2
(45) Date of Patent: Jun. 2, 2015

(54) DEVICE FOR CAPTURE AND LYSIS OF MICROORGANISMS FROM LIQUIDS

(75) Inventors: Kevin Hacker, Cupertino, CA (US);
Gregory Govoni, San Carlos, CA (US);
Nikolay Sergeev, Foster City, CA (US);
Elena Bolchacova, Union City, CA (US); Maxim Brevnov, Union City, CA (US); Manohar Furtado, San Ramon, CA (US); Johnie Young, Daly City, CA (US); Jim Nurse, Pleasanton, CA (US); Mariela Cuadras, San Jose, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/819,240

(22) PCT Filed: Sep. 1, 2011

(86) PCT No.: PCT/US2011/050256
§ 371 (c)(1),
(2), (4) Date: Feb. 26, 2013

(87) PCT Pub. No.: WO2012/031156
PCT Pub. Date: Mar. 8, 2012

(65) Prior Publication Data
US 2013/0157277 A1    Jun. 20, 2013

Related U.S. Application Data

(60) Provisional application No. 61/379,259, filed on Sep. 1, 2010.

(51) Int. Cl.
| | | |
|---|---|---|
| *C12Q 1/68* | (2006.01) | |
| *G01N 21/75* | (2006.01) | |
| *B01D 29/13* | (2006.01) | |
| *C12N 1/06* | (2006.01) | |

(52) U.S. Cl.
CPC  *B01D 29/13* (2013.01); *C12Q 1/68* (2013.01);
*G01N 21/75* (2013.01); *C12N 1/066* (2013.01);
*C12Q 1/689* (2013.01); *C12Q 1/6895* (2013.01)

(58) Field of Classification Search
CPC .................................. G01N 21/75; C12Q 1/68
USPC ............................................ 435/6.1; 422/417
See application file for complete search history.

(56) References Cited

U.S. PATENT DOCUMENTS

| | | | | |
|---|---|---|---|---|
| 5,178,765 | A * | 1/1993 | Hu et al. ...................... | 210/651 |
| 8,574,923 | B2 * | 11/2013 | Cooney et al. ................ | 436/178 |
| 2006/0166347 | A1 | 7/2006 | Faulstich et al. | |
| 2011/0189759 | A1 | 8/2011 | Himmelrich et al. | |

FOREIGN PATENT DOCUMENTS

| | | |
|---|---|---|
| WO | WO-2004/106547 A2 | 12/2004 |
| WO | WO-2007/113583 A1 | 10/2007 |

OTHER PUBLICATIONS

Brevnov, M. et al., "Developmental Validation of the PrepFiler (TM) Forensic DNA Extraction kit for extraction of Genomic DNA from Biological Samples", *Journal of Forensic Sciences*, vol. 54 (3), May 2009, 599-607.

Doebler, R. et al., "Continuous-Flow, Rapid Lysis Devices for Biodefense Nucleic Acid Diagnostic Systems", *Journal of the Association for Laboratory Automation*, vol. 14 (3), Jun. 1, 2009, 119-125.

Lim, et al., "Current and Developing Technologies for Monitoring Agents of Bioterrorism and Biowarfare", *Clinical Microbiology Reviews*, vol. 18, Issue 4,, Oct. 1, 2005, 583-607.

PCT/US2011/050256, , "International Search Report an Written Opinion mailed Dec. 12, 2011", Dec. 12, 2011, 1-11.

* cited by examiner

*Primary Examiner* — Ardin Marschel
(74) *Attorney, Agent, or Firm* — Life Technologies Corporation

(57) ABSTRACT

Devices and methods for detecting microbial contaminants, such as bacteria and fungi, in fluids such as drinking water, pharmaceutical solutions and tissue culture media are provided. More particularly, provided are filtration devices for capture and processing of microorganisms from fluids, and improved methods for recovery, lysis and detection of microorganisms based on a combination of physical disruption with small beads and lysis solutions.

31 Claims, 14 Drawing Sheets

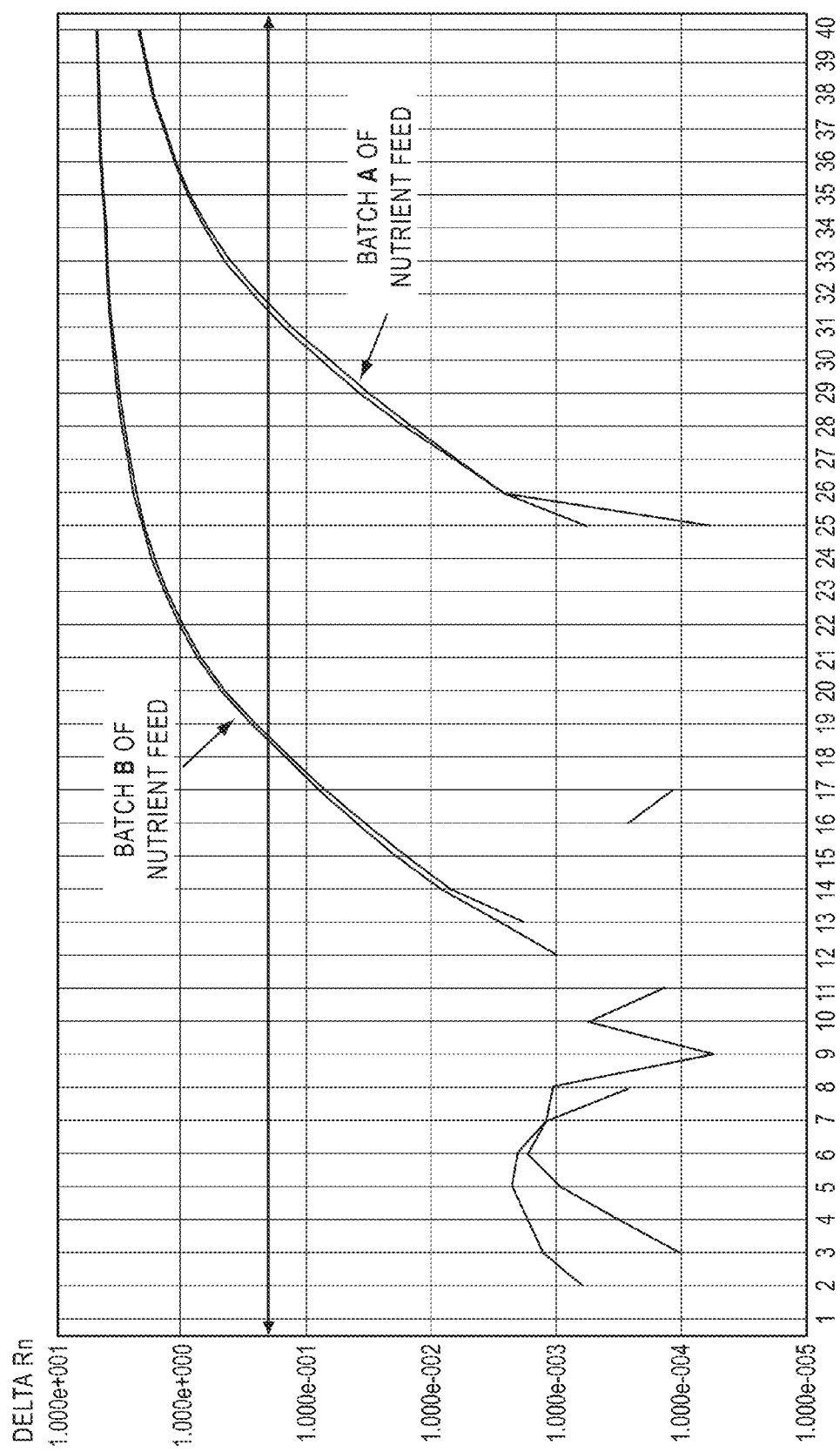

DEVICE FOR CAPTURE AND LYSIS OF MICROORGANISMS FROM LIQUIDS

CROSS REFERENCE TO RELATED APPLICATIONS

This application claims the benefit under 35 U.S.C. 119(e) of U.S. Provisional Patent Application No. 61/379,259, filed Sep. 1, 2010, which is hereby incorporated by reference.

TECHNICAL FIELD

The present invention relates generally to detection of microbial contaminants in fluids such as water, and more specifically to filtration devices for capture of microorganisms and methods for recovery, lysis and detection of microorganisms using such filtration devices.

BACKGROUND

The detection of microbial contaminants, often referred to as "bioburden," is a practice commonly used to ensure the safety, quality, and purity of many fluids encountered in everyday life. Bioburden detection includes monitoring microbial contamination in drinking and industrial water supplies, foods, beverages, research materials (such as tissue culture media), and pharmaceutical preparations. Monitoring is as important to biodefense, where contamination could result from intentional acts of aggression, as it is for industry and consumers, where contamination is typically unintentional.

Traditional methods of determining the presence of contaminating microorganisms in liquids rely on culturing a sample suspected of contamination in a liquid or agar-based medium to increase the number of microorganisms to a detectable level. The sample may be inoculated directly into the culture medium or may first be concentrated by filtration to capture microorganisms for culture. In either case, it may be several days before any microorganism present in the sample can be detected, which can, for example, involve visualizing microbial growth or detecting a byproduct of bacterial metabolism that results in a change in temperature, pH, turbidity, color, bioluminescence, and/or impedance of the culture. Subsequent testing to identify a contaminating microorganism by traditional microbiological methods can add days or weeks to the procedure. Relying on growth in culture requires that an initial educated guess is made of the appropriate culture conditions for an unknown contaminant. Where two or more microorganisms are present in a sample, one may be more suited to the conditions selected (i.e. more "culturable"), resulting in overgrowth of one microorganism, which may obscure the presence of additional organisms in the sample. Consequently in a mixed sample, the presence of some organisms may be overlooked. Pathogenic microorganisms include many that can be "infectious but not culturable" and may therefore go undetected by methods that require a culturing step. For example, certain disinfection-injured bacteria found in the ultra-pure or chlorinated water systems are known to be very difficult to culture.

Thus, there remains a clear need for highly sensitive, rapid and inexpensive devices and methods for detecting bioburden contamination in water treatment and food testing stations, health-care facilities, research laboratories, public buildings and other situations where microbial contamination cannot be tolerated.

SUMMARY

The present disclosure provides a filtration device for capture and lysis of microorganisms from liquids, and methods for capturing, lysing and detecting microorganisms using the provided device. In one aspect, the provided device includes a filter housing consisting of a hollow body defining a fluid path, having an upper input end adapted for receiving a liquid, a lower outflow end, and a filter cavity therebetween; a filter, having an input face and an output face, which is secured within the filter cavity in an orientation perpendicular to the fluid path such that fluid entering the input end of the housing passes through the filter before exiting through the output end, wherein the filter divides the filter cavity into an upper input cavity between the input end of the housing and the input face of the filter, and a lower output cavity between the output face of the filter and the output end of the housing; at least one bead disposed within the input cavity, such that the bead can move freely within the input cavity when the device is agitated; a first sealing means for removably sealing the input end; and a second sealing means for removably sealing the output end. Such sealing means can be, for example, caps or plugs.

In some embodiments, the filter can be a membrane made of a material such as fluorinated aliphatic polymers (such as perfluoro alkoxy, fluorinated ethylene propylene, and Teflon®), polyethersulfone, polysulfone, nylon, nitrocellulose, polyvinylidene fluoride, polytetrafluoroethylene, polypropylene, cellulose acetate, regenerated cellulose, and/or acrylic copolymers. In some embodiments, the typical membrane filter has a nominal pore size of 0.2 μm, has a circular shape and is about 13 mm in diameter.

In some instances, the device includes a support on which the filter rests, which can be, for example, a perforated "shelf" or can include radial protrusions from an inner surface of the output cavity.

In certain embodiments, the at least one bead comprises glass or zirconium, and is typically in the range of about 10 μm to about 100 μm in diameter. Also contemplated is the use of more than one bead, such as a plurality of beads. In some embodiments, where more than one bead is used, they can all be approximately the same size, or the beads can be of different sizes, such as a range of sizes from about 10 μm to about 500 μm in diameter.

In some embodiments, the input cavity, which contains the bead or beads, and in which bead beating occurs, has a generally cylindrical shape and is typically about the same diameter as the filter (e.g. 13 mm). The volume of the input cavity should be sufficient to allow the beads to move and interact with and thereby disrupt, microorganisms in the cavity upon agitation. Typically, the volume of the input cavity will be at least about 2 to about 20 times the volume occupied by the beads. In certain aspects, the depth of the input cavity is at least about 10 to at least about 100 times the diameter of a bead. In some aspects, ridges or baffles can be disposed on an inner surface of the input cavity to increase the turbulence created during bead beating, thereby improving microbial lysis.

In some embodiments, to facilitate filtration of a sample, the input ends of the device can be fitted with luer type connectors that can be connected to syringes, tubing, and other devices having mated connectors. In certain aspects, the input end includes a female luer fitting and the output end includes a male luer fitting such that the device can be connected to a syringe or a can be connected in-line to a vessel containing a sample for analysis.

In another aspect, methods are provided for detecting and/or identifying a microbial contaminant in a liquid, such as water, a cell culture medium, a pharmacological solution or a biological solution, using a filter unit described herein. Accordingly, the liquid may be a liquid to be tested for the presence of a microorganism or a liquid containing contaminant microorganisms. According to such methods, a sample of liquid is filtered through the device, such that the microorganisms are captured by the device filter. Optionally, the filter is washed with a sterile liquid to remove non-microbial contaminants that may interfere with subsequent detection steps. The output end of the device is then sealed to prevent loss of solution, and a lysis solution is dispensed onto the filter in an amount sufficient to cover the filter.

The lysis solution can be any solution that will facilitate microbial lysis, but will advantageously have at least some independent ability to lyse bacteria or fungi. In some embodiments, the lysis solution is a PCR-compatible lysis solution. An exemplary detergent-based lysis solution includes n-lauroyl sarcosine sodium, sodium deoxycholate, and Tween-20.

After sealing the input end of the filter unit, the device is agitated to effect bead beating of the microorganisms captured by the filter. The bead beating step will typically cause at least one bead to strike the membrane, a captured microorganism, an inner surface of the device or a combination thereof, thereby disrupting and forming a lysate of the captured microorganisms. Optionally, following addition of the lysis solution, the filter unit can be heated to a temperature between 50° C. and 90° C. prior to bead beating to enhance lysis.

Following the bead beating step, the lysate is recovered from the device (e.g. by centrifugation into a microfuge tube). In some embodiments, the beads are also recovered with the lysate and a second bead beating step is performed in the recovery tube. In such embodiments, the second bead beating step may help to disrupt unlysed microorganisms that remain and improve detection.

Finally, an assay to detect or identify the presence or absence of a nucleic acid of a captured microorganism in the lysate is performed, the presence of the nucleic acid indicating a microbial contaminant in the liquid.

In some embodiments, detecting a nucleic acid in the lysate is by a polymerase chain reaction (PCR) assay. The PCR assay can detect either an RNA or a DNA molecule of the microorganism, e.g. by standard, reverse transcriptase, real-time or quantitative PCR.

Through the appropriate choice of PCR primers, both individual types of bacteria and fungi can be detected, as well as more general detection of fungi and/or bacteria. For example, the provided methods can be used to test for the presence or absence of a specific type of bacteria or fungus, by performing PCR in the presence of single pair of primers that each amplifies a specific nucleic acid present only in that single type of bacteria or fungus. Alternatively, pan-fungal and/or pan-bacterial primers can be used to amplify similar or identical nucleic acid sequences present in a variety of, or in all types of bacteria or fungi. A similar effect may be achieved by including a plurality of primer pairs in the PCR reaction.

Using the provided methods under the optimized conditions described herein, as few as 2 bacteria or 20 fungi can be detected in a large volume of liquid (i.e. 1 to 300 mL).

BRIEF DESCRIPTION OF THE DRAWINGS

FIG. 13A and FIG. 13B illustrate detection of fungal contamination in nutrient feed samples. FIG. 13A shows the result of samples tested using the capture, lysis and PCR method provided. FIG. 13B is an image of a culture plate showing the result of the nutrient feed batch A tested using the direct plating method.

DETAILED DESCRIPTION

Figure 1:
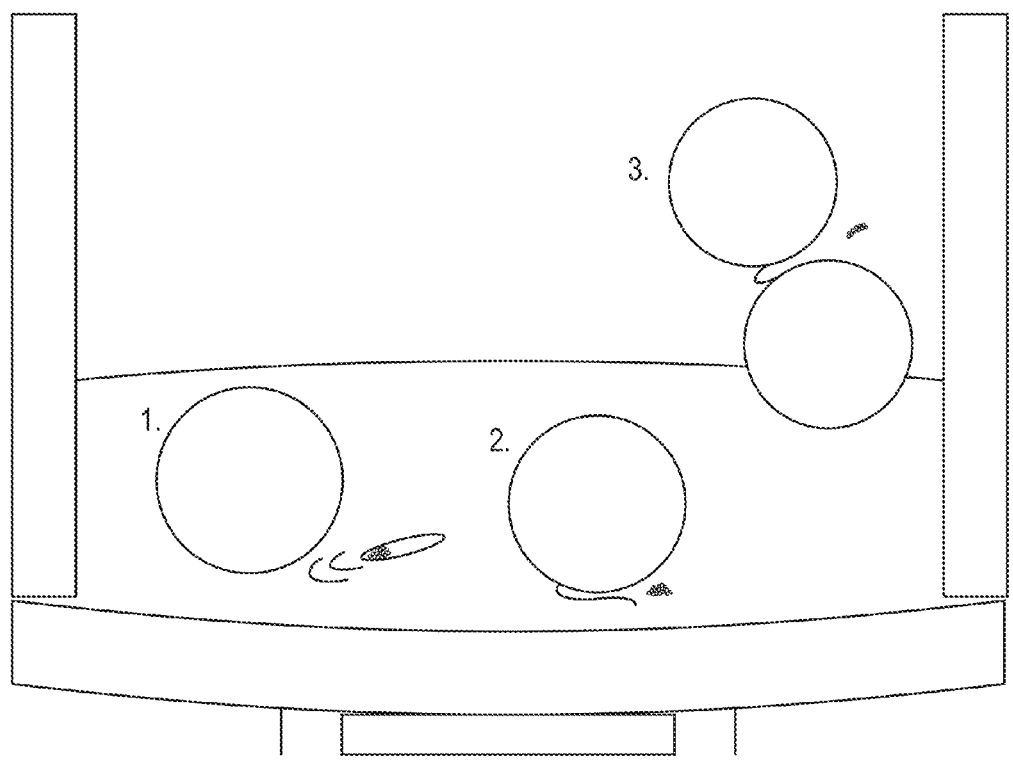
FIG. 1 is an illustration of possible mechanisms of microorganism resuspension and lysis in a filter unit of the disclosure during bead beating.

It is to be understood that both the foregoing general description and the following detailed description are exemplary and explanatory only and are not restrictive of the invention claimed. As used herein, the use of the singular includes the plural unless specifically stated otherwise.

Unless specific definitions are provided, the nomenclatures utilized in connection with, and the laboratory procedures and techniques of molecular biology, microbiology, biochemistry, and organic chemistry described herein are those known in the art. Standard chemical and biological symbols and abbreviations are used interchangeably with the full names represented by such symbols and abbreviations. Thus, for example, the terms "deoxyribonucleic acid" and "DNA" are understood to have identical meaning. Standard techniques may be used e.g., for chemical syntheses, chemical analyses, recombinant DNA methodology, and oligonucleotide synthesis. Reactions and purification techniques may be performed e.g., using kits according to manufacturer's specifications, as commonly accomplished in the art or as described herein. The foregoing techniques and procedures may be generally performed according to conventional methods well known in the art and as described in various general or more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)); Ausubel et al., Current Protocols in Molecular Biology (John Wiley & Sons Inc., N.Y. (2003)), the contents of which are incorporated by reference herein in their entirety for any purpose.

"About" as used herein means that a number referred to as "about" comprises the recited number plus or minus 1-10% of that recited number. For example, "about" 50 nucleotides can mean 45-55 nucleotides or as few as 49-51 nucleotides depending on the situation. Whenever it appears herein, a numerical range, such as "45-55", refers to each integer in the given range; e.g., "45-55%" means that the percentage can be 45%, 46%, etc., up to and including 55%. Where a range described herein includes decimal values, such as "1.2% to 10.5%", the range refers to each decimal value of the smallest increment indicated in the given range; e.g. "1.2% to 10.5%" means that the percentage can be 1.2%, 1.3%, 1.4%, 1.5%, etc. up to and including 10.5%; while "1.20% to 10.50%" means that the percentage can be 1.20%, 1.21%, 1.22%, 1.23%, etc. up to and including 10.50%.

As used herein, "or" means "and/or" unless stated otherwise. Furthermore, use of the term "including" as well as other forms, such as "includes," and "included," is understood as "comprising" and is not limiting. The section headings used herein are for organizational purposes only and are not to be construed as limiting the subject matter described.

The present disclosure is based in part on the observation that physical disruption with small (e.g. about 10-100 µm diameter) glass or zirconia beads (also referred to as "bead beating"), in the presence of a detergent-based lysis buffer, is effective for dislodging cells from the membrane of a filter unit and lysing the cells to expose the cell contents (e.g. nucleic acids) for analysis. Moreover, the beads can be added directly to a filtration device used to collect microorganisms and the entire assembly can be mixed to effect cell lysis and recovery from the device.

Without wishing to be bound by a particular theory, FIG. 1 illustrates possible mechanisms of microorganism resuspension and lysis in a filter unit during bead beating. A cross section of an exemplary filter unit is shown, with the housing of the filter unit in gray and the filter membrane shown within the filter unit in the lower half of the Figure. Microbial cells are represented by ovals, with a small scribbles indicating nucleic acid within the cell or released therefrom. Beads are indicated by the large gray circles. Three types of possible bead-cell interactions are indicated by numerals 1, 2 and 3. Interaction 1. depicts a microorganism being dislodged from a filter and/or being resuspended by the turbulence created when a bead lands near the microorganism. Interaction 2. shows lysis of a microorganism captured on the filter when it is forcefully contacted by a bead. Interaction 3. shows a microorganism colliding with two beads, the impact of which crushes the microorganism trapped between the two beads, thereby lysing the microorganism.

Thus, in one embodiment, provided a device for capture and lysis of microorganisms from a liquid. The device, which is also referred to herein as a "filter unit," includes a filter housing, which is a generally hollow body defining a fluid path, having an upper input end adapted for receiving a liquid, a lower outflow end, and a filter cavity therebetween; and a filter, having an input face and an output face, which is secured within the filter cavity perpendicular to the fluid path such that fluid entering the input end of the housing must pass through the filter before exiting the output end. The filter thereby divides the filter cavity into an upper input cavity between the input end of the housing and the input face of the filter, and a lower output cavity between the output face of the filter and the output end of the housing. The device also includes at least one bead disposed within the input cavity such that the bead can move freely within the input cavity, and may also include means for sealing the input and output ends of the device, such as caps or plugs.

A detergent-based lysis solution is used to lyse the captured microorganisms during bead beating. The lysis solution can be any solution that will facilitate microbial lysis, and in particular, will have at least some independent ability to lyse bacteria or fungi. Detergent-based lysis solutions suitable for lysing microorganisms are well known in the art.

In some embodiments, the lysis solution need not be compatible with PCR. When a lysis solution incompatible with PCR is used, steps can be taken following bead beating to remove or substantially reduce any PCR inhibitors in the lysate, including, but not limited to, purification of nucleic acids from the lysate before a PCR amplification.

In some embodiments, the lysis solution is a PCR-compatible lysis solution. PCR-compatible lysis solutions are commercially available and detergents compatible with PCR and other nucleic acid amplification reactions are well known in the art. Exemplary PCR-compatible detergents include ionic detergents, such as sodium deoxycholate and n-lauroyl sarcosine sodium, and nonionic detergents, such as Triton® X-100, Nonidet® P-40, Tween® 20, and octylphenoxypolyethoxyethanol glycol (IGEPAL® CA-630). Concentrations of such detergents for use in PCR-compatible lysis solutions are known in the art and can range, for example from about 0.01% to about 0.6%. See, for example, *Principles and Applications for DNA Amplification,* 1989, Erlich et al., ed., Stockton Press; Bachman et al. (1990) *Nucleic Acids Res.* 18:1309; Goldenberg et al. (1995) *PCR Methods and Applications* 4:368-370.

Accordingly, in one embodiment, the detergent-based lysis solution contains at least one detergent of the group consisting of sodium deoxycholate, n-lauroyl sarcosine sodium, Triton® X-100, Nonidet® P-40, Tween® 20, and IGEPAL® CA-630. In another embodiment, the detergent-based lysis solution contains at least two detergents of the group consisting of sodium deoxycholate, n-lauroyl sarcosine sodium, Triton® X-100, Nonidet® P-40, Tween® 20, and IGEPAL® CA-630. In another embodiment, the detergent-based lysis solution contains at least three detergents of the group consisting of sodium deoxycholate, n-lauroyl sarcosine sodium, Triton® X-100, Nonidet® P-40, Tween® 20, and IGEPAL® CA-630. In certain embodiments, such lysis solutions are PCR-compatible.

"Beads," as used herein, refers to small particles of a generally spherical shape, that are typically made of a dense, inert material such as glass, silica, zirconia, silicon carbide and combinations thereof. Such beads are commercially available. Metal beads, (e.g. steel, such as stainless steel or chrome steel) are also contemplated for use in the devices and methods provided. The beads may be uniform in size or may be a mixture of sizes, but are typically in the range of about 1 µm to about 1 mm in diameter, frequently about 5 µm to about 500 µm in diameter, and are often about 10 µm to about 100 µm in diameter. Smaller beads (e.g. about 10-100 µm diameter) may be more suitable for use with bacterial samples, while larger beads (e.g. about 200 µm or larger) may be necessary to lyse fungal samples. Where the microorganism is unknown, it may be desirable to include a mixture of bead sizes. In certain aspects, the beads of the devices and methods provided may be smooth. However, more efficient lysis of certain microorganisms may be achieved when the beads include irregularities or are rough, grooved, and/or sharp, such as beads that include zirconia or silicon carbide. Tougher, more lysis-resistant microorganisms may also benefit from exposure to beads of a higher density material, such as zirconia, which is 100% denser than glass.

Exemplary zirconia beads for use in the filter unit and methods provided herein include, without limitation, zirconium oxide beads (e.g., 95% $ZrO_2$), zirconia silica beads ($ZrO_2+SiO_2$), magnesium-stabilized zirconium oxide beads (ZrO+MgO stabilizer), yttrium-stabilized zirconium oxide beads (e.g., 95% $ZrO_2$+5% $Y_2O_3$), and rare earth-stabilized zirconium oxide beads ($ZrO_2$+CeO).

In some embodiments, beads for use in the provided filter unit and methods have a diameter of about 10 μm to about 800 μm. In certain embodiments, the beads are about 50 mm, about 100 μm, about 200 μm, about 300 μm, about 400 μm, about 500 μm, about 600 μm, about 700 μm, or about 800 μm in diameter. In certain embodiments, the beads have a diameter of about 10 μm to about 500 μm. In some embodiments, a mixture of at least two bead sizes are used. In other embodiments, a mixture of at least three bead sizes are used. For example, in one embodiment, a mixture of bead sizes from about 10 μm to about 100 μm are used. In other embodiments, a mixture of bead sizes from about 50 μm to about 200 μm, from about 100 μm to about 200 μm, or from about 200 μm to about 400 μm are used.

In some embodiments, the beads are washed prior to assembly into the filter unit and/or use in the detection method, for example, to improve microorganism detection and/or identification. In some embodiments, such pre-washing of the beads reduces PCR inhibition associated with use of unwashed beads and renders the beads and filter device more compatible with PCR. The beads may be washed with aqueous solutions including, but not limited to, water, mild acid, buffered solutions such as Tris-EDTA and lysis solution, and/ or phosphate buffered saline (PBS). In some embodiments, beads are pre-washed with HCl solutions, such as 0.25-2.0 N HCl. In certain embodiments, beads are pre-washed with 0.25 N, 0.5 N, 0.75 N, 1.0 N, 1.25 N, 1.5 N, 1.75 N or 2.0 N HCl.

In some embodiments, the beads and/or interior of the filter unit is treated so as to inhibit growth of any organisms and/or remove potentially detectable nucleic acids that may be on component surfaces. For example, hypochlorite (bleach) may be used to inhibit organism growth and disintegrate detectable lengths of nucleic acid in the filter unit.

In some embodiments, the beads are sterilized prior to assembly into the filter unit. Autoclaving at 120° C. for about 45 minutes or heating at 200° C. for about 1 hour are typical procedures for sterilization of beads. The skilled artisan will be familiar with other such treatments.

The housing of the filter unit of the disclosure can be made of any material or combination of materials that can be formed into the desired water-tight shape and will not degrade or deform under the conditions of the methods described herein. Typically, the filter housing is plastic, such as polystyrene, polypropylene, acrylic, polyvinyl chloride, high density polyethylene, polycarbonate, epoxy or combinations thereof. Typically the filter and housing together will be a single-use, disposable item and will be sterile. However, reusable housings are also contemplated, such as housings made from stainless steel. In such embodiments, the housing may be formed of two or more parts that can be disassembled for cleaning, and then reassembled with a replacement filter prior to reuse. Such parts may, for example, have mated connections, such as screw-type threads, or may be friction fitted. As will be appreciated by the skilled artisan, coatings, gaskets or other adaptations and modifications of the housing connections may be necessary to prevent fluid leakage during use.

"Membrane," "membrane filter," and "filter" are used interchangeably to refer to a thin, microporous material having pores of a specified nominal diameter (i.e. pore size) so as to prevent the passage of particles, such as microorganisms, of greater particular size than a the pore. Suitable membranes for capturing bacteria and fungi based are known in the art. The membrane must be sufficiently strong to withstand the mechanical forces from bead beating without tearing and have a nominal pore size that retains the microorganism(s) present in the sample. The membranes for use in the provided devices and methods will generally have a pore size in the range of about 0.1 μm to about 0.45 μm, and typically have pores of about 0.2 μm. In some embodiments, membranes having a smaller pore size, such as small as 20-100 nm may be used. Any material compatible with the reagents and solutions that are passed through the membrane can be used, including but not limited to, fluorinated aliphatic polymers such as perfluoro alkoxy (PFA), fluorinated ethylene propylene (FEP) and Teflon®, nylon, nitrocellulose, polysulfone, polyvinylidene fluoride (PVDF), polyethersulfone (PES), polytetrafluoroethylene (PTFE), cellulose acetate, polypropylene, polyester, cellulose ester, regenerated cellulose, acrylic copolymers, and the like. Membranes may be treated, for example, to improve strength, resistance to chemical or physical degradation and to minimize adsorption of biomolecules, such as proteins. In certain embodiments, the membrane has low binding of protein and other macromolecules to avoid retention of unwanted species which could cause blockage of the filter and/or interfere with subsequent PCR reactions. Low protein binding is particularly important when the solution tested for microbial contamination contains proteins, such as serum, cell culture media, and certain biological preparations for intravenous administration. In one aspect, the membrane is made of polyethersulfone (PES) which is hydrophilic, has low protein binding and is stable in alkaline pH.

Conveniently, the input and output ends of the device provided herein can include luer type fittings for connection to mated syringes, tubing, i.v. bags and other similar devices. For example, in one embodiment, the input end may include a female luer or luer-lock fitting that can be connected to a male luer-type fitting of a syringe. The syringe can be filled with a sample fluid and the sample dispensed directly into the filter unit via the syringe. For larger volumes, the input end of the filter unit can be connected to a sample-containing vessel with tubing and pumped though the filter unit by applying positive pressure. When the output end of the filter unit is connected to tubing, negative pressure can be applied thereto for drawing sample fluid through the filter unit.

In yet further embodiments, the sample can be pipetted or otherwise dispensed directly through the open input end of the filter unit and allowed to pass through the membrane by gravity. For faster processing, the sample can be centrifuged through the filter. The skilled artisan will be familiar with additional methods for sample application.

The surface area and composition of the filter will dictate the amount of sample that can be passed through a single filter unit. In use, it is not expected that the capacity of the filter for capturing microorganisms would be exceeded. However, the filter may become clogged with non-microbial contaminants, such as proteins, lipid, particulate matter and the like. In certain aspects, particulates can be removed by passage through a glass fiber or other suitable pre-filter prior to microorganism capture by the filter unit.

Figure 5:
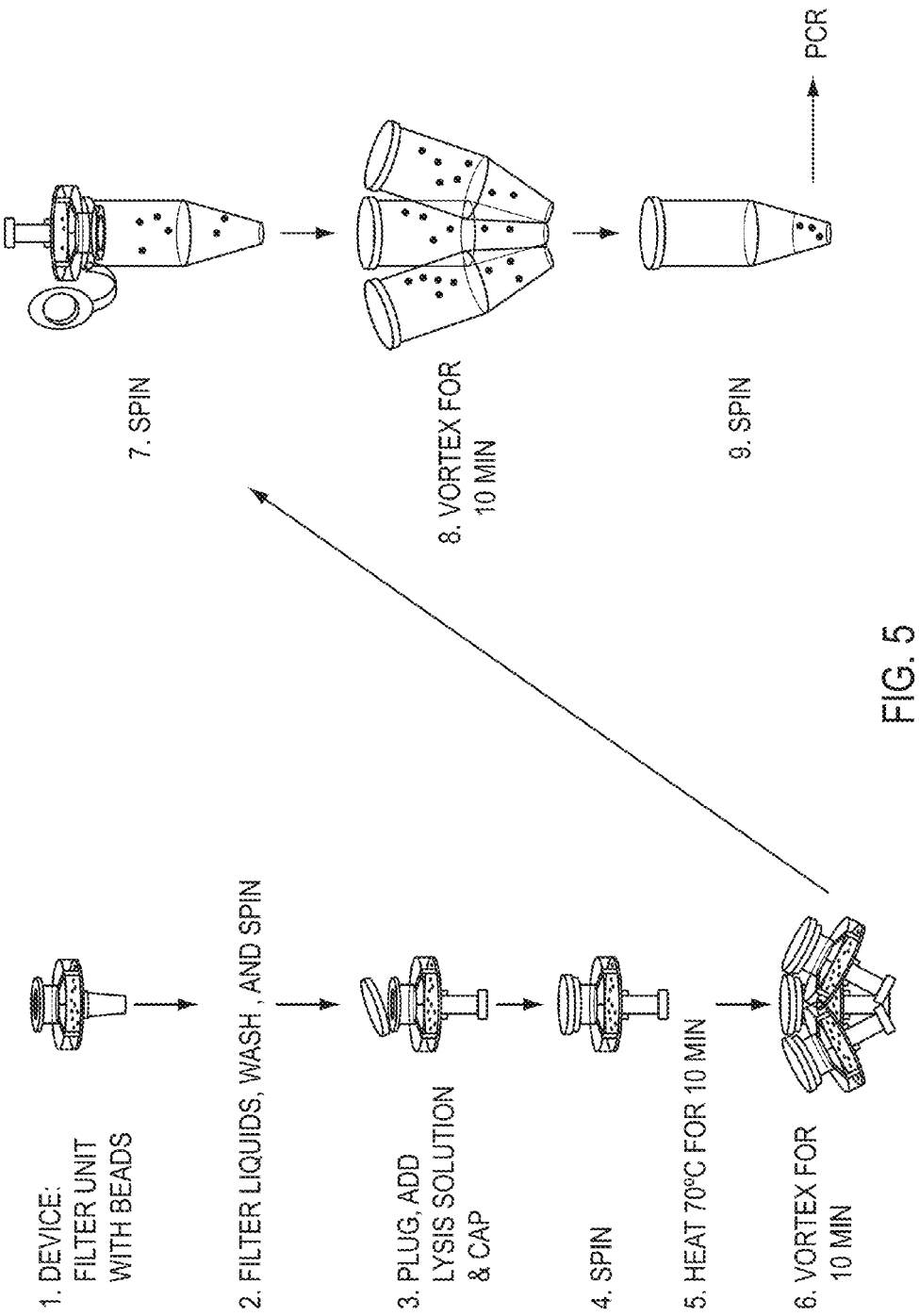
FIG. 5 illustrates a provided filter unit and a method of use for capturing and recovering microbial contaminants from a liquid that includes dual bead beating steps.

The device can be any shape, but typically has a cylindrical shape overall. In certain embodiments, the device fits within a standard centrifuge tube, such as a microfuge tube or a 15 mL or 50 mL capacity centrifuge tube (e.g., Corning No.: 430055 or No.: 430304). In other non-limiting embodiments, the device is sized and shaped to rest on top of a standard centrifuge tube. For example, either or both of the input end or output end can have a diameter that fits within a microfuge tube, while the filter cavity has a diameter larger than the tube, allowing the filter unit to rest on top of the tube as illustrated in FIG. 5 (7).

Figure 2:
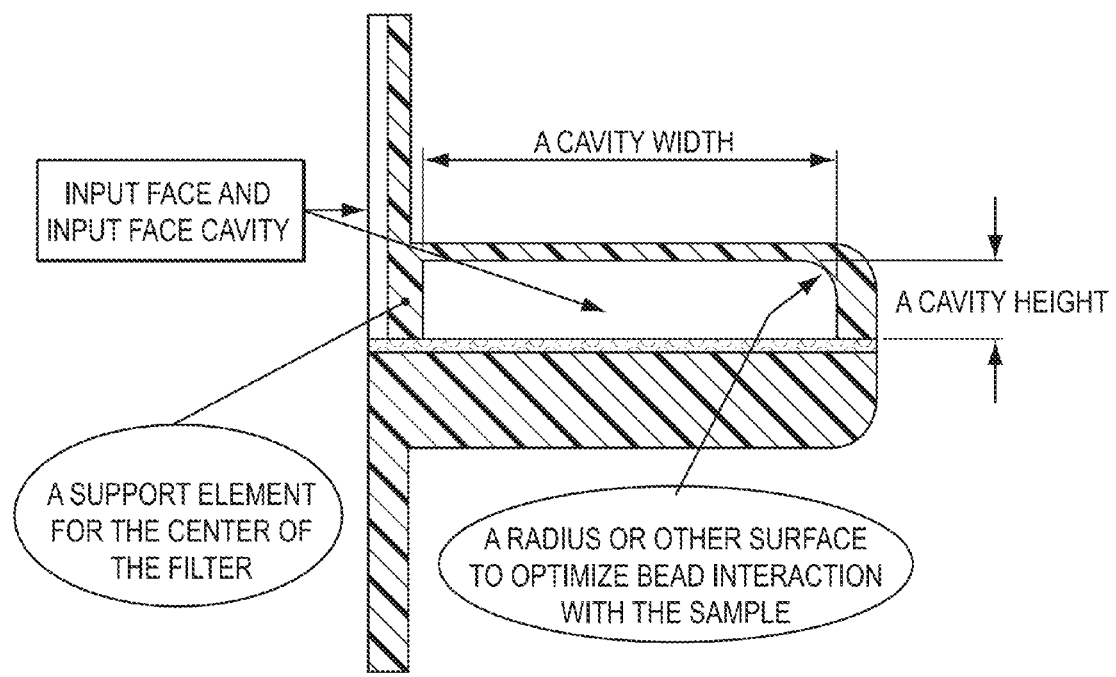
FIG. 2 is a cross-sectional view of a filter unit of the disclosure.
Figure 3:
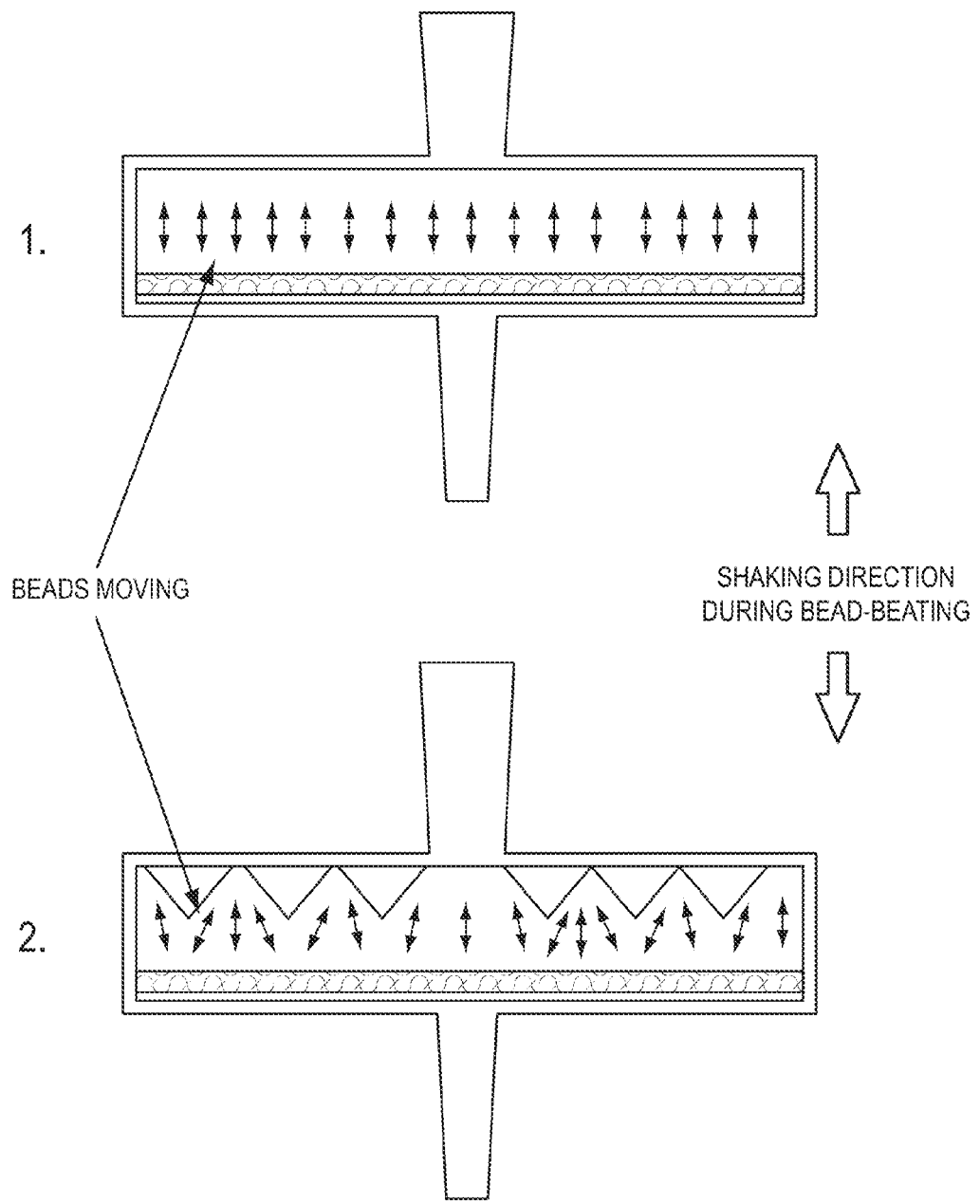
FIG. 3 illustrates the movement of beads in provided filtration devices with and without baffles.

The filter cavity typically has a cylindrical shape overall, but may include a radial inner surface (FIG. 2) or other internal geometries to maximize lysis and recovery of microorganisms. To increase the efficiency of mechanical lysis by increasing the dispersal of beads and turbulence generated during bead beating, ridges, baffles or the like, may be disposed on an inner surface of the input cavity as shown in FIG. 3 (2.).

In certain embodiments, the filter cavity is sized to accommodate standard circular filters of 13 mm, 25 mm or 47 mm diameter. The input cavity of the filter unit is of sufficient volume to accommodate the beads and at least a small volume of sample or lysis solution. In use, bead beating takes place within the input cavity. Thus, it is desirable to provide sufficient space for the beads to move around within this cavity, as illustrated in FIG. 2 and FIG. 3 (1.). In certain aspects, the depth of the input cavity is at a least about 10 times the diameter of the at least one bead. In other embodiments, the depth of the input cavity is at least about 100 times the diameter of the bead. In yet other embodiments, a plurality of beads are contained within the input cavity, which cavity has a volume at least about 2, at least about 5, at least about 10 or at least about 20 times the volume of the beads.

The filter unit may also include one or more supports for the membrane to prevent displacing, distorting or tearing of the filter during bead beating. In one aspect, the filter support is a perforated circular element, which is secured underneath the filter (i.e. adjacent to the output face of the filter). In other embodiments, filter support is provided by one or more radial protrusions from an inner surface of the housing.

During the bead beating step(s) of the provided methods, agitation of the filter unit is performed to effect lysis of captured microorganisms. Suitable agitation means and methods, such as vigorous shaking, vortexing and the like, to effect such lysis are known and will be familiar to the skilled artisan.

Figure 4:
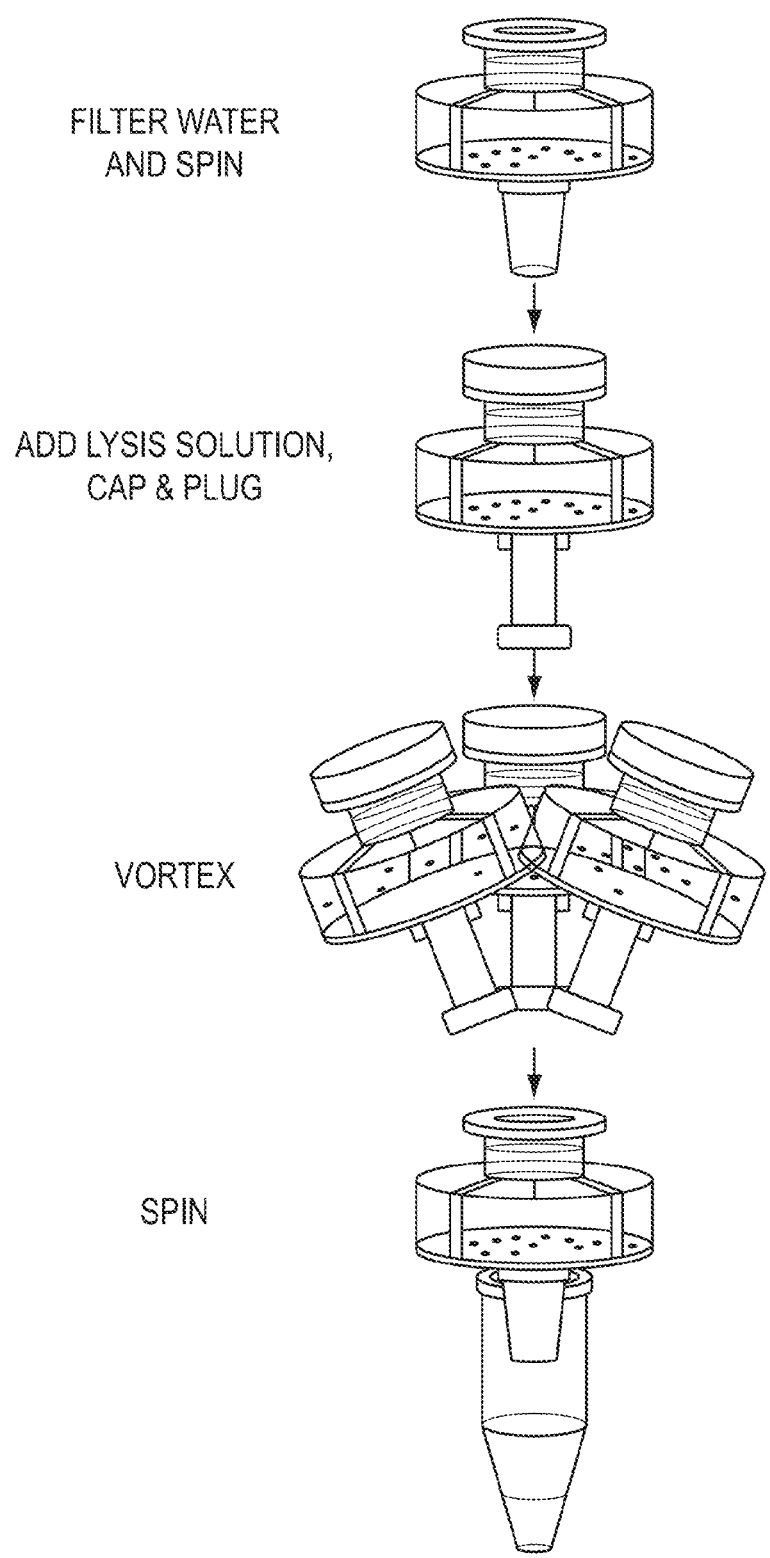
FIG. 4 illustrates a provided filter unit and a simplified method of use for capturing and recovering microbial contaminants from a liquid.

FIG. 4 illustrates one embodiment of the provided filter unit, where the device has a suitable space above the membrane for optimal bead beating of the retained microorganisms. In use, a microorganism-containing sample, or a sample to be tested for the presence of microorganisms, is applied to the device, and filtered by centrifugation (FIG. 4, top). The microorganisms retained on the filter are then lysed in the presence of a PCR-compatible, detergent-based lysis solution and vortexed to effect bead beating. (FIG. 4, center). The lysed microorganisms are then recovered from the filter unit by centrifugation (FIG. 4, bottom).

Also provided are methods for recovering, lysing, and detection and/or identification of microorganisms in a liquid. An example of one such method is illustrated in FIG. 5. A filter unit as provided herein containing beads of approximate size of 100 μm (1) is used in this embodiment. A syringe or other device is used to dispense a sample fluid into the filter unit device, which passes through the 0.2 μm filter in the filter unit. (2) Bacteria and fungi present in the sample fluid are retained by the filter. If the liquid contains PCR inhibitors, a brief wash (e.g., with water) can be performed. The liquid remaining in the filter unit is removed by a brief spin in a centrifuge. (3) A plug is added to the bottom of the filter unit to minimize the volume of PCR-compatible lysis solution needed to cover the top of the filter membrane. A small amount of PCR-compatible lysis solution, such as 30 μL for a 13 mm filter, is added and (4) the filter unit is briefly centrifuged to evenly cover the filter membrane with the lysis solution. (5) Optionally, the filter unit is capped and placed in a 70° C. incubator to aid in the lysis of microorganisms. (6) Bead beating is effected by vortexing or vigorous shaking the capped unit, which lyses the microorganisms. (7) The cap and plug are removed, the filter unit is inverted over a collection tube and spun upside up to recover the lysis solution containing the microorganisms into the collection tube. Along with intact and lysed microorganisms, the beads are also dispensed into the collection tube. (8) To further lyse the microorganisms in the lysis solution, the collection tube is vortexed to bead beat unlysed microorganisms. Finally the tube is briefly spun to separate the beads from the lysis mixture (lysate). An aliquot (e.g. 12 μL of an original 30 μL volume of lysis solution) of the mixture is removed and added to 18 μL of PCR reagents containing pan-bacteria and pan-fungi primers, and PCR is performed to detect the microorganisms.

Figure 6:
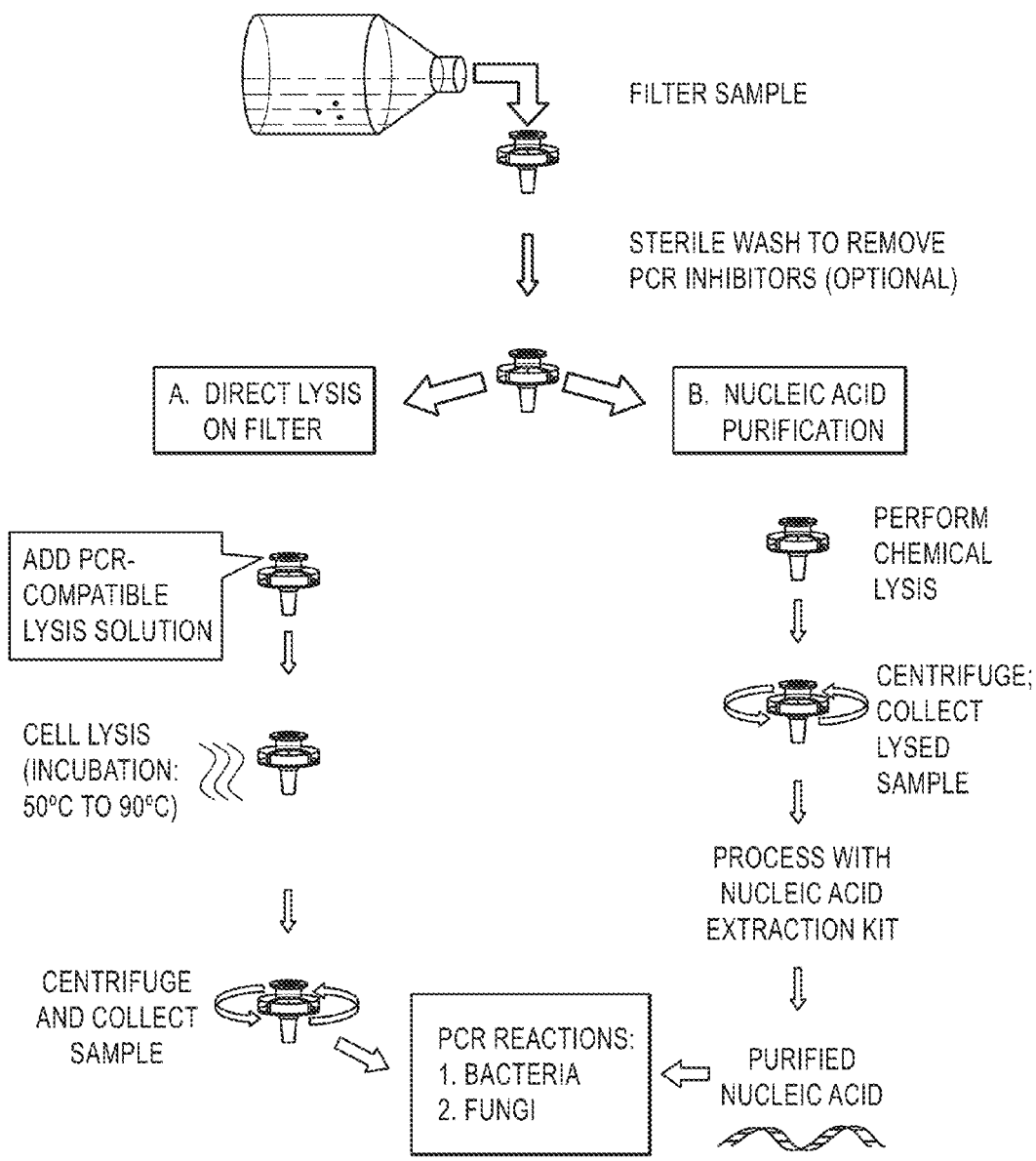
FIG. 6 illustrates alternative methods for capturing and recovering microbial contaminants from a liquid.

FIG. 6 compares additional exemplary methods using the provided filter units to capture and lyse microorganisms and prepare the lysed samples for detection by PCR. According to these methods, a sample solution is passed through a filter unit as described above to capture microorganisms. Optionally, the filter is washed with a sterile solution, such as water, to remove PCR inhibitors. The captured microorganisms can then be lysed directly on the filter through the combination of detergent-based PCR-compatible lysis solution and bead beating (A), or by chemical lysis of the captured microorganisms according to methods known in the art (B). Direct, on-filter lysis includes the addition of a PCR-compatible lysis solution to the filter device in sufficient volume to cover and soak the membrane and ensure efficient lysis. Optionally, the device together with the lysis solution can be incubated at an elevated temperature (e.g. about 50° C.-about 90° C.) to enhance the lysis efficiency. The combination of detergent, (which may alone be sufficient to lyse some microorganisms) and bead beating provides an effective means to recover and disrupt most bacteria and fungi. After lysis, the filter device is centrifuged to collect the lysate into a microfuge tube and cellular debris is pelleted by further centrifugation. The cleared lysate can then be added directly to a PCR reaction mixture containing bacterial- and/or fungal-specific primer pairs and amplified using polymerase chain reaction (PCR) for example, using a real-time PCR instrument, to detect the presence of bacteria and fungi.

Some samples, such as those that contain inhibitors of PCR, high lipid content or particulates may require nucleic acid purification from the captured microorganisms prior to detection, which may be achieved using methods known in the art, as outlined in FIG. 6, B. On-filter lysis can be included in this method to reduce sample loss. Thus, this method also provides the sensitivity required for the detection of small numbers of microorganisms. Chemical and/or enzymatic lysis reagents that are known in the art (e.g. lysozyme, β-glucanase, alkali, sodium dodecyl sulfate, guanidine HCl) are added directly to the filter device and heated to increase efficiency of lysis. The filter unit is then be centrifuged to collect the lysates and nucleic acid is extracted and purified prior to amplification and detection of bacterial- and fungal-specific sequences as in method A.

As used herein the term "sample" refers to a liquid, or a liquid derived from a starting material, suspected of harboring a microorganism or group of microorganisms. Examples of samples include, but are not limited to, pharmaceutical samples, biopharmaceutical samples, food samples or samples derived from food (including but not limited to samples from food intended for human or animal consumption such as processed foods, raw food material, produce (e.g., fruit and vegetables), legumes, meats (from livestock animals and/or game animals), fish, sea food, nuts, beverages, drinks, fermentation broths, and/or a selectively enriched food matrix comprising any of the above listed foods), samples from food processing and manufacturing surfaces, water samples, environmental samples or samples derived therefrom (e.g., soil samples, dirt samples, garbage samples, sewage samples, industrial effluent samples, air samples, or water samples from a variety of water bodies such as lakes, rivers, ponds etc.,), liquid samples derived from air samples (from the environment or from a room or a building), forensic samples, agricultural samples, and/or biological samples (e.g., from eukaryotic or prokaryotic sources). Examples of eukaryotic sources include mammals, such as a human, a cow, a pig, a chicken, a turkey, a livestock animal, a fish, a crab, a crustacean, a rabbit, a game animal, and/or a murine animal such as rat or mouse. A biological sample may include blood, urine, feces, or other materials from a human or a livestock animal. A biological sample can be, for instance, in the form of a single cell, in the form of a tissue, or in the form of a fluid.

A sample may be directly introduced into a filter device of the disclosure for capture and lysis of a microbial contaminant. However, in some embodiments a sample may be prepared or processed in some manner prior to filtration by the filter device. For example, for food samples, a portion of food or a swabbed sample is typically combined with an appropriate liquid, such as water, a buffer solution, or a culture medium such as a selective medium or an enrichment medium to enrich a microorganism contaminant therein. In some embodiments, food is chopped, macerated, liquefied, diced, or homogenized. In some embodiments, large volumes of sample, for example, but not limited to, volumes of 100 mL, 250 mL, or more are processed or a portion of the food or beverage and appropriate liquid are typically combined to form a dilute suspension, for example but not limited to, ratios of about 1:5, 1:10, or 1:20 (w/vol). In some embodiments, a detergent, an emulsifying agent, or both, is added to enhance the solubility of high lipid foods, for example but not limited to butter and certain other dairy products. In certain embodiments, 25 grams of a solid or semi-solid food is combined with 225 mL of a suitable culture media. In some embodiments, 25 mL of a beverage or a liquefied or partially liquefied food is combined with 225 mL of a suitable culture media.

Food samples may also be pooled to save on testing costs, e.g., instead of testing 15×25 g samples of food, a composite of 375 g, with 25 g coming from different lots of food are tested. If any composite is tested positive, then the individual 15 samples are further evaluated. If the composite is negative, then the food testing lab has saved the cost of 15 individual tests.

In some embodiments, the sample comprises a pharmaceutical or biopharmaceutical solution, or solutions from pharmaceutical or biopharmaceutical manufacturing. Accordingly, in some embodiments, the sample to be tested for microbial contamination is a cell culture medium collected at any time point in the cell culture process, for example, before cell addition, during cell culture, and after cell culture (e.g., post-fermentation). In certain embodiments, the sample includes unconcentrated harvest media or concentrated harvest media, such as an ultra-filtrate harvest media. As such, the sample to be tested may contain a high protein content or residual cells or cell debris. In some embodiments, the sample may be a biopharmaceutical or pharmaceutical product at an intermediate stage in manufacture or at a final product stage. Samples may also include raw materials used in pharmaceutical manufacturing, including without limitation water, buffer solutions, and solvents.

The following examples are provided by way of illustration and not by way of limitation.

EXAMPLES

Example 1

Analysis of Bacillus cereus Contamination of Water

Figure 7:
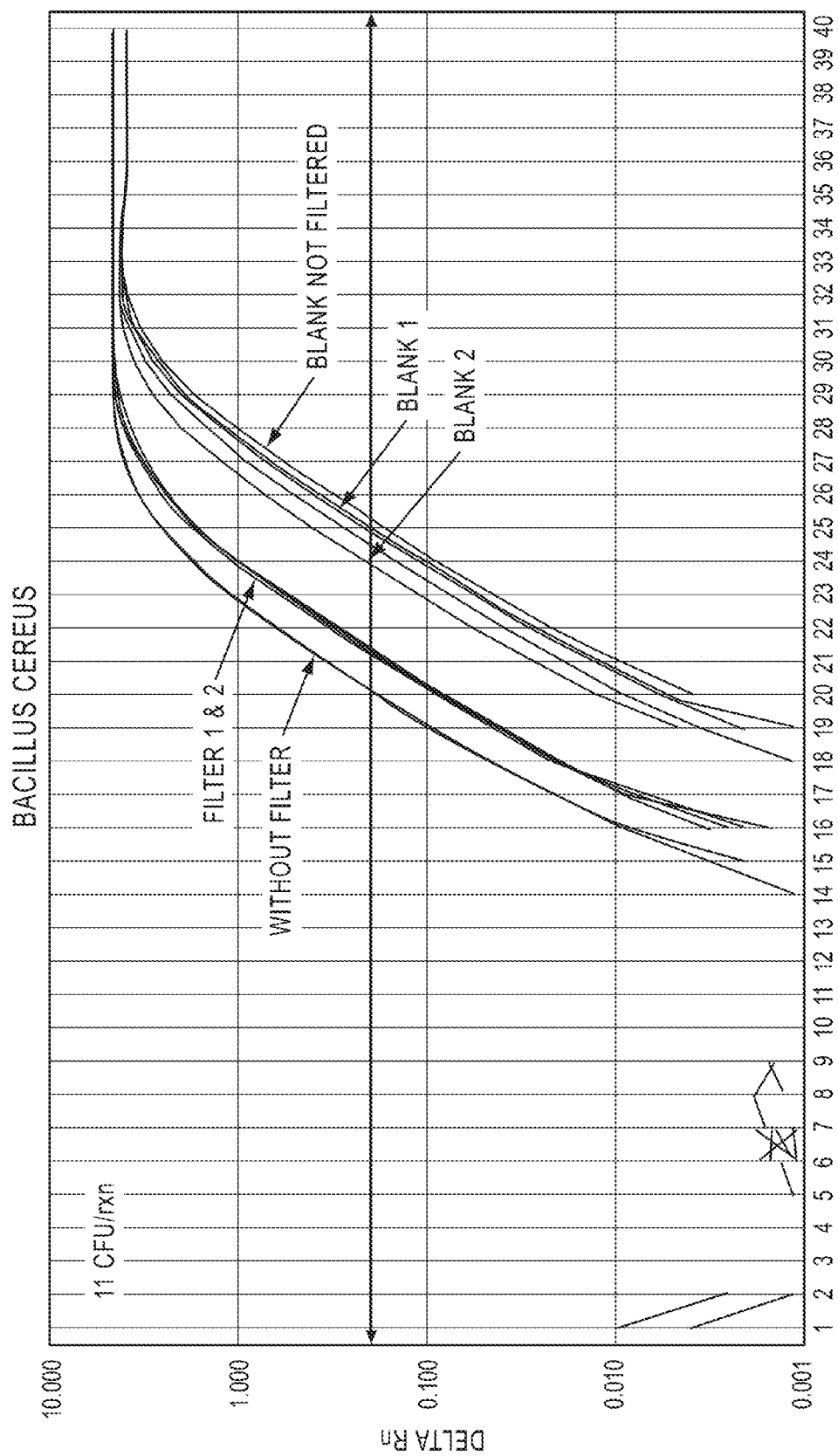
FIG. 7 illustrates the detection of *Bacillus cereus* in water using a method provided herein.

Approximately 200 colony forming unites (CFUs) of Bacillus cereus were spiked into several 1 mL samples of sterile water. The samples were passed through a membrane filter unit equipped with a 0.2 micron pore size filter. After air drying the membrane filter, 100 µL of a PCR-compatible lysis solution (0.05% (w/v) N-lauroyl sarcosine sodium, 0.025% (w/v) sodium deoxycholate, 0.05% (v/v) Tween® 20, 1% (v/v) Glycerol, and 0.1 mM EDTA) was added to the filter device, which was then incubated at 70° C. for 5 minutes to promote lysis of captured microorganisms. The filter unit was centrifuged to recover the sample lysate in a microfuge tube. Five µL of the collected sample lysate ($\frac{1}{20}^{th}$ of the sample) was then added to a PCR reaction mixture (Power SYBR® Green PCR Master Mix, Life Technologies) containing a primer pair for amplification of a B. cereus nucleic acid sequence. Contaminated water samples without filtration were processed in parallel to assess filter capture. Sample blanks for filtered and non-filtered workflow solutions were used as controls to detect background contamination for the system, which was observed to be non-significant. Based on cycle threshold data, greater than 46% of the contaminant was recovered as compared to non-filter control (FIG. 7).

Example 2

Analysis of Burkholderia cepacia Contamination of Water

Figure 8:
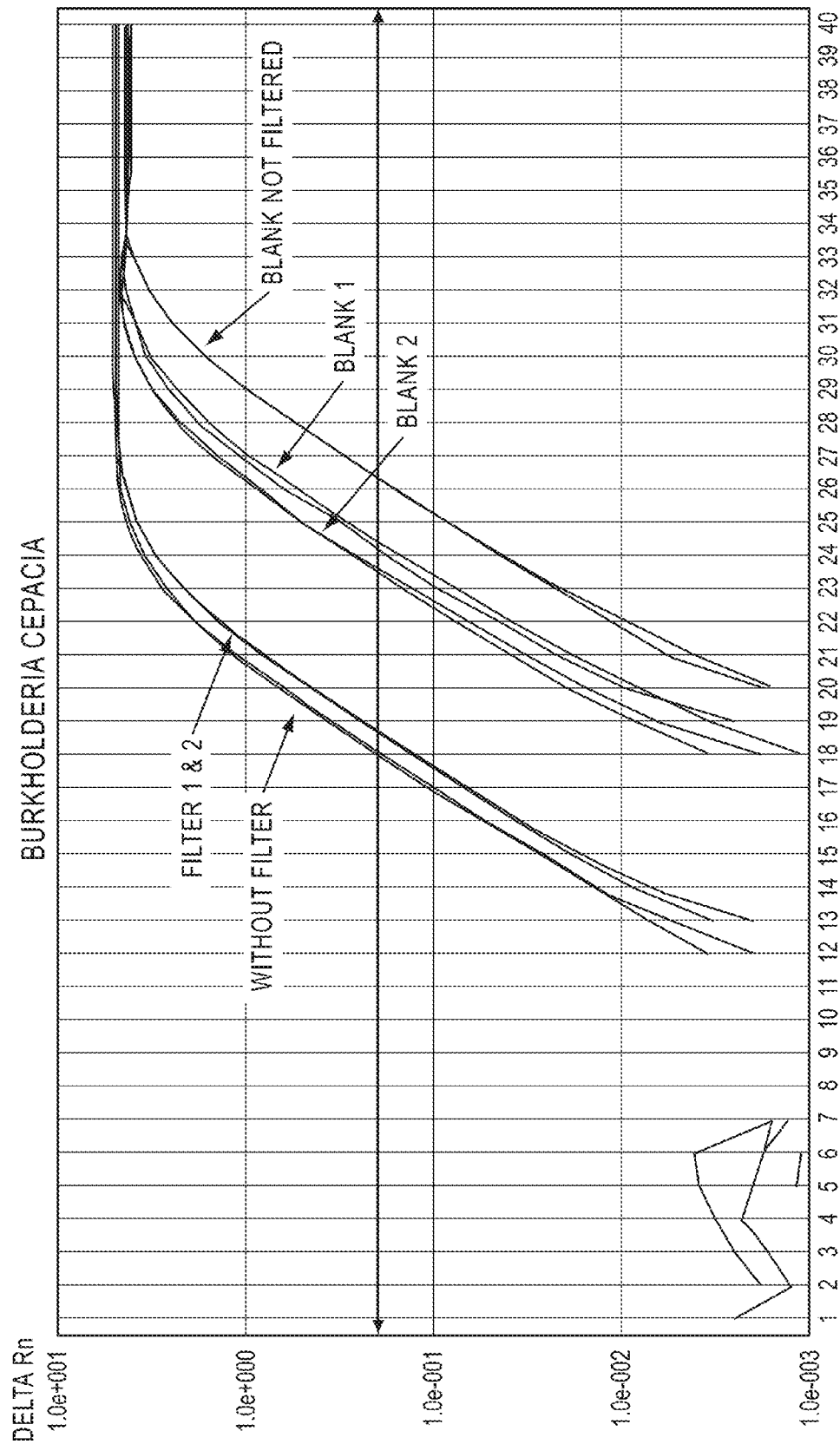
FIG. 8 illustrates the detection of *Burkholderia cepacia* in water using a method provided herein.

Approximately 1000 CFUs of Burkholderia cepacia were spiked into several 1 mL samples of sterile water. The samples were then processed in the same manner as described above in Example 1 to assess filter recovery. Based on cycle threshold data, greater than 65% of the contaminant was recovered with on-filter recovery as compared to non-filtered control. (FIG. 8).

Example 3

Figure 9:
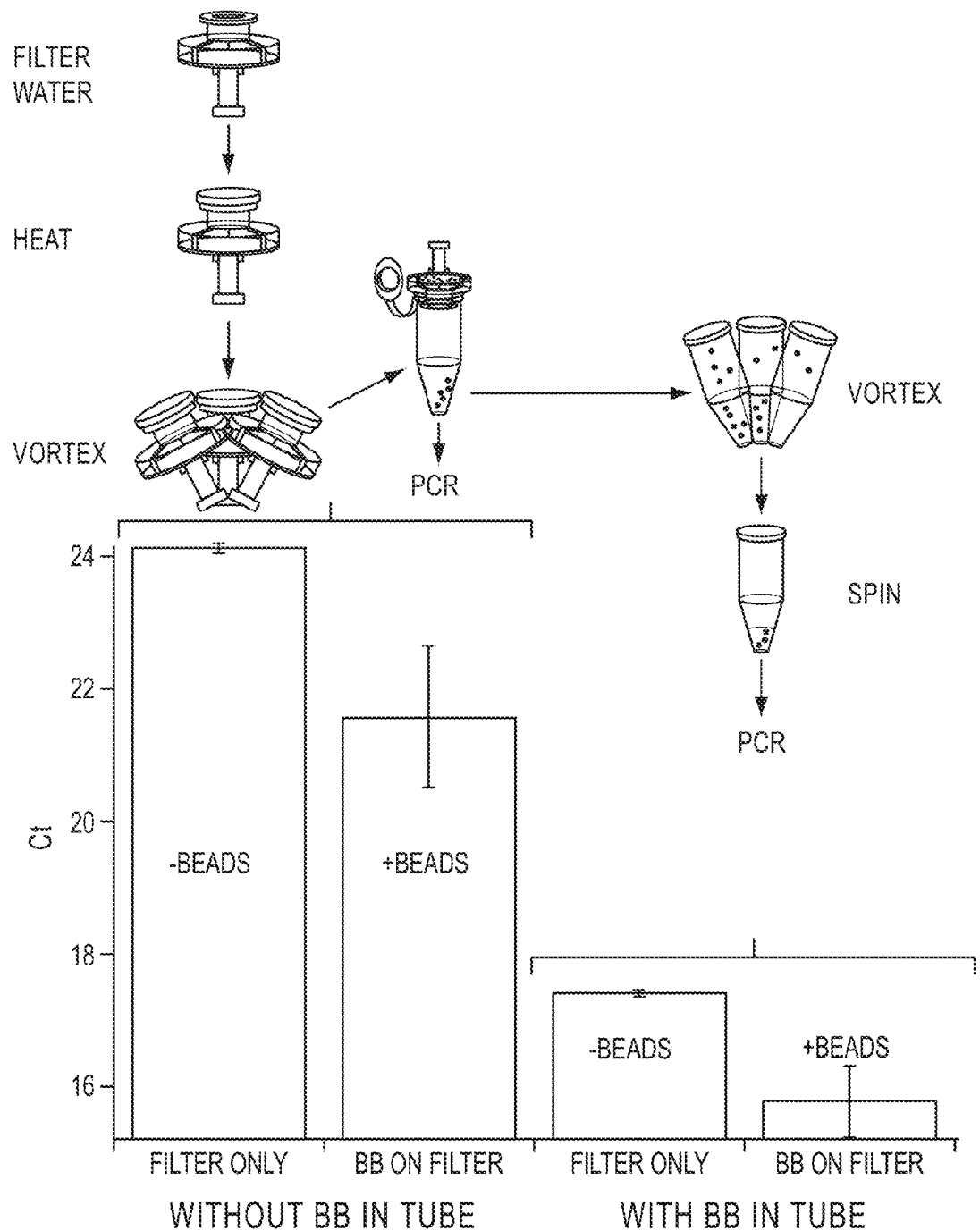
FIG. 9 illustrates the effect of single and dual bead beating (BB) on the detection of *Aspergillus* in water using a method provided herein.

Detection of Aspergillus Using Filter Capture and Dual Bead Beating Recovery and Lysis Aspergillus was spiked into several 1 mL samples of sterile water. The samples were passed through a membrane filter unit and captured microorganisms were lysed as described above in the previous Examples, except that some samples included zirconium beads (100 µm) and were vortexed prior to lysate recovery (bead beaten samples). Following lysate recovery, duplicate samples containing beads were processed in parallel, with some samples receiving an additional vortex/bead beating in the recovery tube. As shown in FIG. 9, the inclusion of two bead beating steps (on the capture filter and in the recovery tube), resulted in a significantly improved the sensitivity of Aspergillis detection. The first two columns show that bead beating in the filter unit lyses fungi. However, the lowest cycle threshold (Ct) is observed when both bead beating steps are performed.

Example 4

Figure 10:
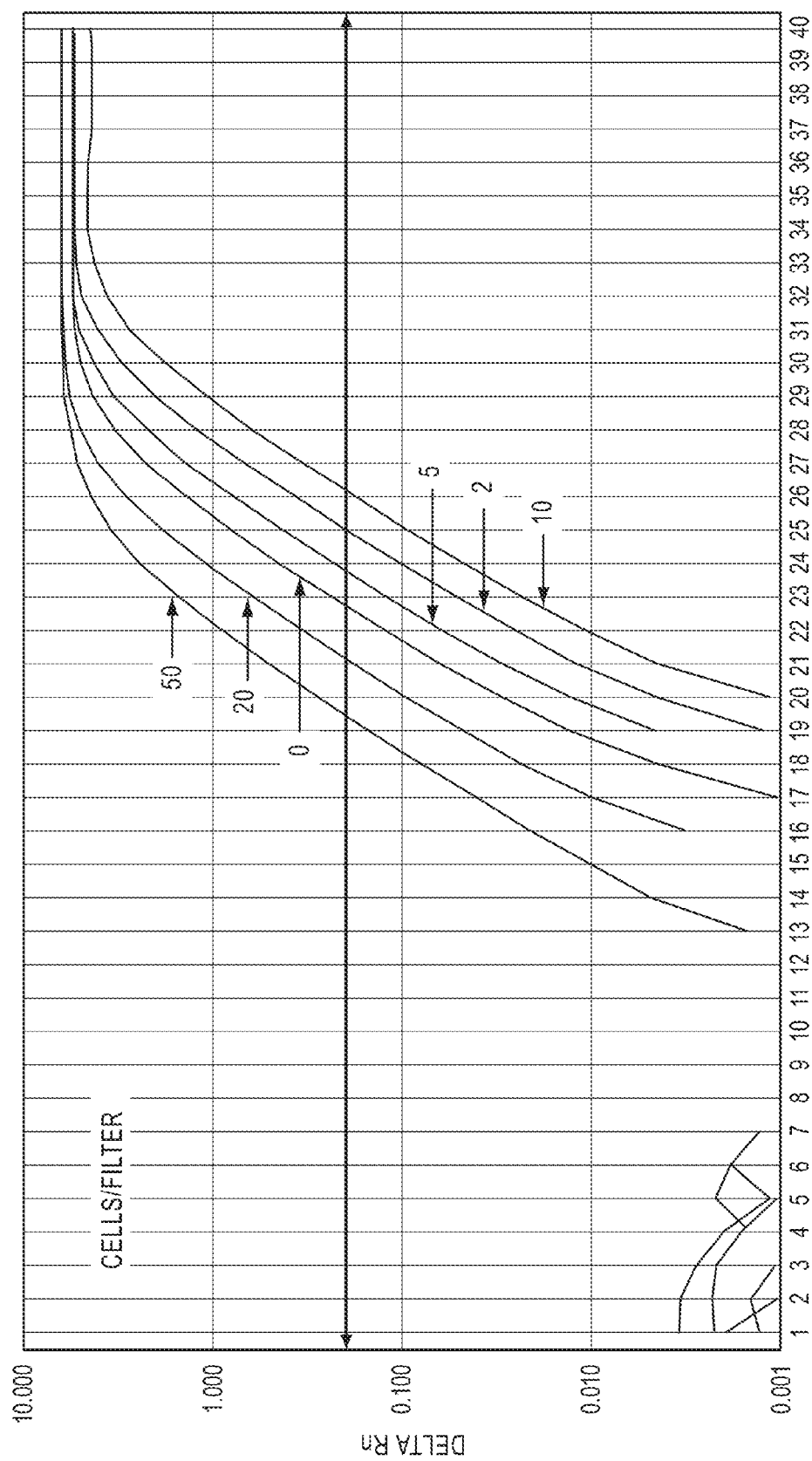
FIG. 10 illustrates the detection of *Candida albicans* in contaminated water using a method provided herein.

Detection of Candida albicans Using Filter Capture and Dual Bead Beating Recovery and Lysis Candida albicans was spiked into several 20 mL samples of "sterile" water. The samples were filtered, lysed and recovered as described above in Example 3, including two bead beating steps. The lysates were processed for detection of *C. albicans* by Q-PCR using pan-fungi specific primers. As shown in FIG. 10, the sample containing 0 cells/filter represents no *C. albicans* added to the 20 mL sample of water that was filtered in this experiment. The low Ct for the "0" sample suggested that the water could be contaminated with fungi. Analysis of samples using native agarose gel electrophoresis supported this conclusion (data not shown). Even with water containing an unknown number of unidentified microorganisms, 50 and 20 *C. albicans* cells spiked into the water could be detected (FIG. 10).

Example 5

Figure 11:
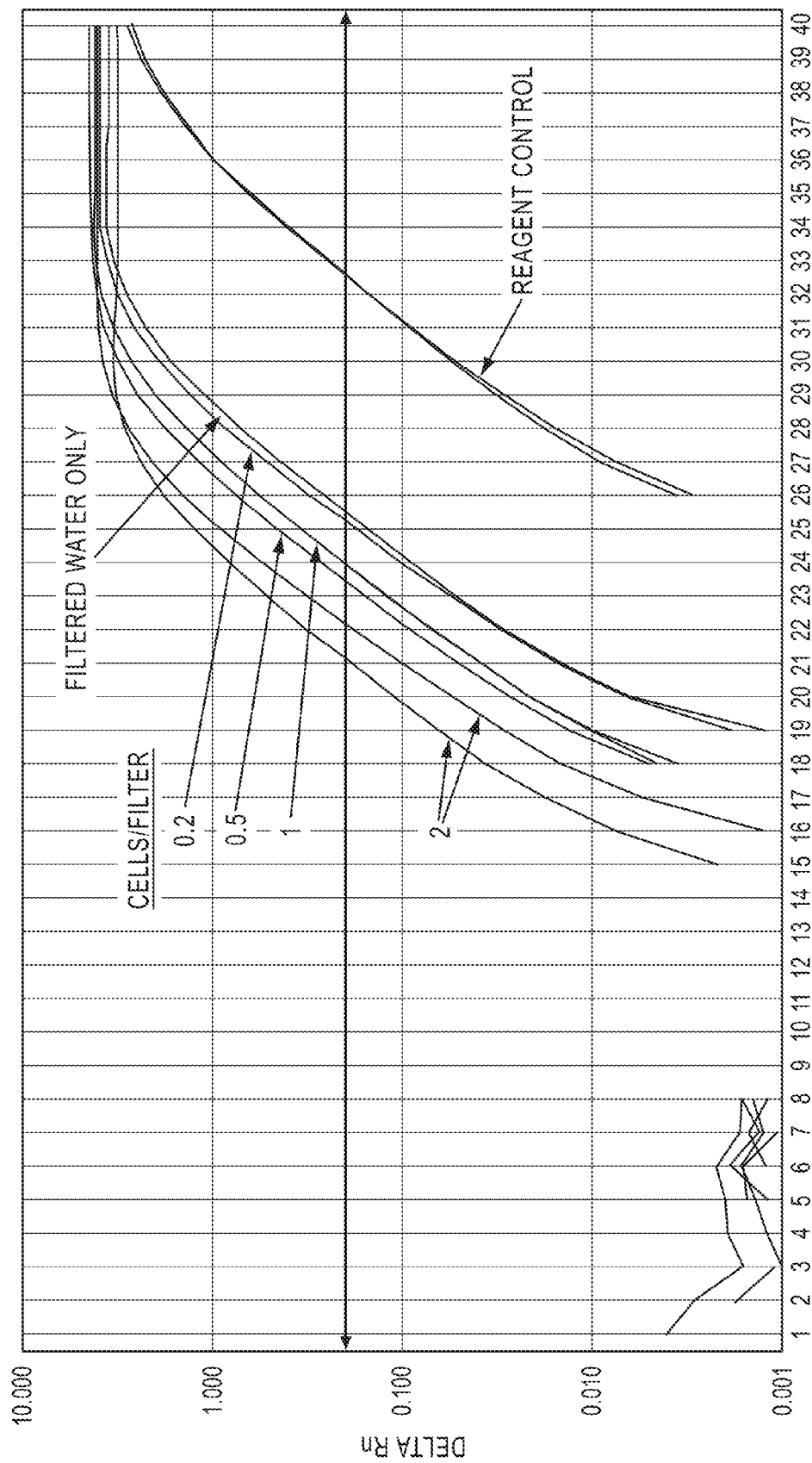
FIG. 11 illustrates the detection of *Bacillus cereus* in contaminated water using a method provided herein.

Detection of *Bacillus cereus* Using Filter Capture and Dual Bead Beating Recovery and Lysis Various amounts of *Bacillus cereus* was spiked into several 20 mL samples of water. The samples were filtered, lysed and recovered as described above in Examples 3 and 4 above, including two bead beating steps. The lysates were processed for detection of bacterial nucleic acids by Q-PCR using pan-bacterial specific primers as described above. The same contaminated water used in Example 4 was used in this experiment. As shown in FIG. 11, 2 CFU of *B. cereus* could be detected from 20 mL.

Example 6

Detection of Bacterial Contamination in Detergent Sample

Figure 12:
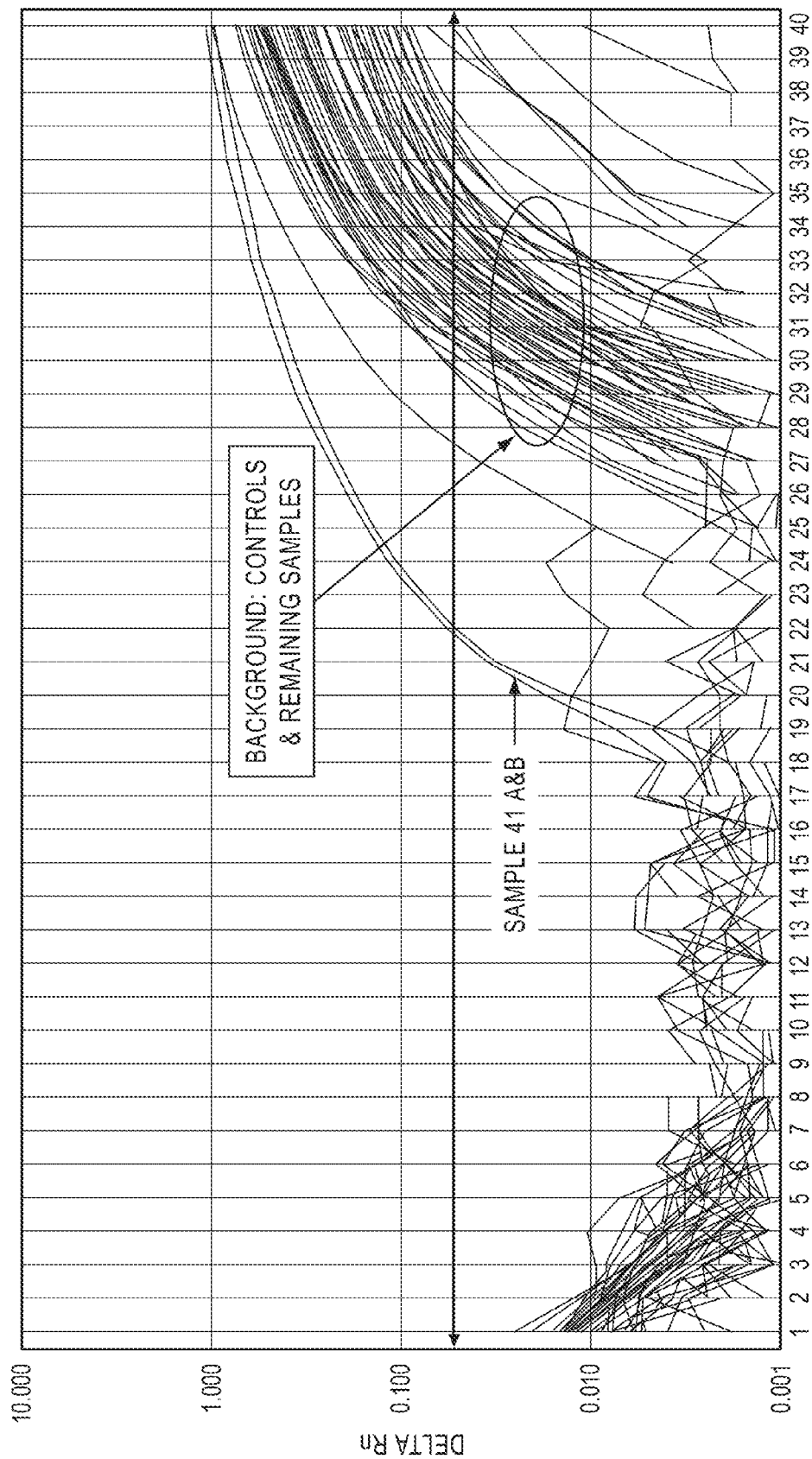
FIG. 12 illustrates the detection of bacterial contamination in Tween® 20 samples using a method provided herein.

One half milliliter of Tween-20 was diluted into a total of 10 mL of 10 mM Tris-HCl buffer, pH 8.0, containing 0.1 mM EDTA (low TE buffer). The samples were passed through a membrane filter unit equipped with a 0.2 micron pore size filter, the device was washed by filtering two 10 mL aliquots of low TE buffer, and residual fluid was drained by a brief centrifugation. Then, 100 µL of a PCR-compatible lysis solution was added to the filter device and the filter device was vortexed at 3000 rpm for 10 minutes. The filter device was centrifuged to recover the lysate in a microcentrifuge tube and the collected sample lysates were tested with a total bacterial count assay in RNA detection format. For this, 5 µL of the collected sample lysate ($\frac{1}{20}^{th}$ of the sample) was then added to an RT-PCR reaction mixture containing SYBR® Green dye (Life Technologies Corp.) and primer pairs for amplification of 16S ribosomal RNA. Samples of phosphate buffered saline, pH 7.4 (PBS), and uncontaminated Tween-20 were used as controls to detect background contamination for the system, which was observed to be non-significant. Based on cycle threshold (Ct) data, a large amount of microbial RNA was present in the contaminated Tween-20 sample (FIG. 12, Samples 41 A & B); Table 1).

TABLE 1

| Sample | Ct | RNA amount (fg/PCR rxn) |
|---|---|---|
| PBS control | 33.3 | 11.4 |
| Tween-20 (contaminated) (Samples 41 A & B) | 26.1 | 1322.4 |
| Tween-20 (clean) | >40 | Not determined |

Example 7

Detection of Fungal Contamination in Nutrient Feed

Figure 13B:
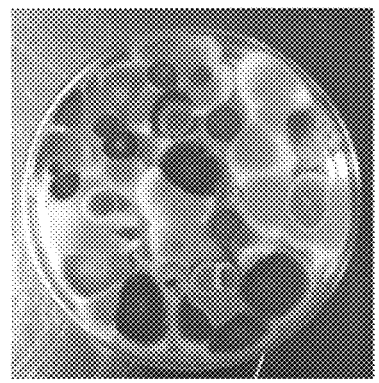

Two batches of powdered nutrient feed (the component of cell culture media) were tested for inherent fungal contamination. Powdered media was dissolved in 50 mM Tris-HCl, pH 8.0, according to manufacturer recommendations. Ten milliliters of nutrient feed was filtered through a membrane filter unit equipped with a 0.2 micron pore size filter, the device was washed by filtering two 10 mL aliquots of low TE buffer, and residual fluid was drained by a brief centrifugation. Then, 100 µL of a PCR-compatible lysis solution was added to the filter device and the filter device was vortexed at 3000 rpm for 10 minutes. The filter device was centrifuged to recover the lysate in a microcentrifuge tube and the collected sample lysates were tested with a universal fungal assay, detecting fungal 18S rDNA genes. For this, 5 µL of the collected sample lysate ($\frac{1}{20}^{th}$ of the sample) was then added to a PCR reaction mixture (Power SYBR® Green PCR Master Mix, Life Technologies Corp.) containing primer pairs for amplification of universal region of 18S rDNA gene. As shown in FIG. 13A and Table 2, the assay results show a clear difference between contaminated and non-contaminated batches of nutrient feed. Direct plating of 0.5 mL of nutrient feed Batch A confirmed fungal contamination (FIG. 13B).

TABLE 2

| Nutrient Feed | DNA quantity (in fg) per gram nutrient feed | | |
|---|---|---|---|
|  | Device 1 | Device 2 | Average |
| Batch A | 4 fg | UD | 4 fg |
| Batch B | 104,260 fg | 148,750 fg | 126,380 fg |

Example 8

Cell Culture Media Testing

Figure 14:
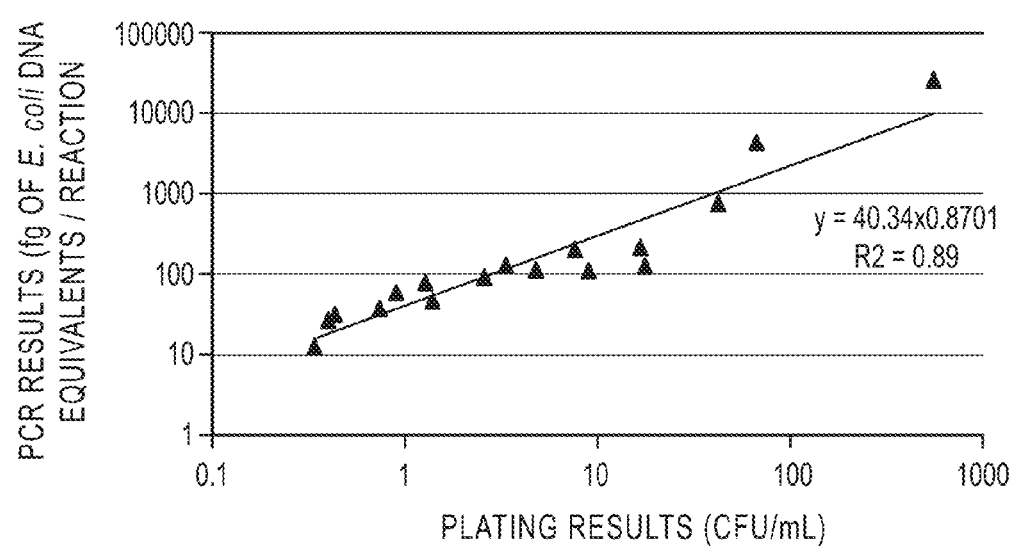
FIG. 14 illustrates the correlation between the provided capture, lysis and PCR method and the plating method in testing for bacteria in cell culture media.

Over a 3 month period, synthetic cell culture media (media containing components supporting cell growth) samples were obtained and tested for inherent bacterial contamination. Ten milliliters of culture was filtered through a membrane filter unit equipped with a 0.2 micron pore size filter, the device was washed by filtering two 10 mL aliquots of PBS, and residual fluid was drained by a brief centrifugation. Then, 100 µL of a PCR-compatible lysis solution was added to the filter device and the filter device was vortexed at 3000 rpm for 10 minutes. The filter device was centrifuged to recover the lysate in a microcentrifuge tube and the collected sample lysates were tested with a pan-bacterial assay, detecting 16S rDNA genes. For this, 5 µL of the collected sample lysate ($\frac{1}{20}^{th}$ of the sample) was then added to a PCR reaction mixture (Power SYBR® Green PCR Master Mix, Life Technologies) containing a primer pairs for amplification of universal regions of bacterial 16S rDNA gene. A plating assay was used to determine bacterial colony forming units (CFU) from each cell culture sample. As shown in FIG. 14, the assay results show a linear correlation between culturable CFU/mL and DNA detectable by the capture and lysis method (fg DNA/reaction).

All publications and patents mentioned in this specification are herein incorporated by reference to the same extent as if each individual publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A device for capture and lysis of microorganisms from a liquid comprising:
    a) a filter housing consisting of a hollow body defining a fluid path, having an upper input end adapted for receiving a liquid, a lower outflow end, and a filter cavity therebetween;
    b) a filter, having an input face and an output face, secured within the filter cavity in an orientation perpendicular to the fluid path wherein the filter is configured such that fluid can enter the input end of the housing and then pass through the filter before exiting the output end, wherein the filter divides the filter cavity into an upper input cavity between the input end of the housing and the input face of the filter, and a lower output cavity between the output face of the filter and the output end of the housing;
    c) at least one bead disposed within the input cavity, wherein the bead can move freely within the input cavity when the device is agitated and the bead is about 10 µm to about 100 µm in diameter;
    d) a first sealing means for removably sealing the input end, wherein the first sealing means is selected from a cap and a plug; and
    e) a second sealing means for removably sealing the output end, wherein the second sealing means is selected from a cap and a plug.

2. The device of claim 1, wherein the input end comprises a female luer fitting.

3. The device of claim 1, wherein the output end comprises a male luer fitting.

4. The device of claim 1, wherein the filter is a membrane made of a material selected from the group consisting of polyethersulfone, polysulfone, nylon, nitrocellulose, polyvinylidene fluoride, polytetrafluoroethylene, polypropylene, cellulose acetate, regenerated cellulose, acrylic copolymers, perfluoro alkoxy, fluorinated ethylene propylene, and Teflon®.

5. The device of claim 4, wherein the membrane has a nominal pore size of 0.2 µm.

6. The device of claim 4, wherein the membrane has a circular shape and is about 13 mm in diameter.

7. The device of claim 6, wherein the input cavity has a generally cylindrical shape and is about 13 mm in diameter.

8. The device of claim 6, wherein the depth of the input cavity is at least about 10 times the diameter of the at least one bead.

9. The device of claim 6, wherein the depth of the input cavity is at least about 100 times the diameter of the at least one bead.

10. The device of claim 1, further comprising a support disposed within the output cavity upon which the filter rests.

11. The device of claim 10, wherein the support is a perforated element adjacent to the output face of the filter.

12. The device of claim 10, wherein the support comprises at least one radial protrusion from an inner surface of the output cavity.

13. The device of claim 1, wherein the at least one bead comprises glass or zirconium.

14. The device of claim 1, wherein the at least one bead consists of a plurality of beads.

15. The device of claim 14, wherein the plurality of beads are about the same size.

16. The device of claim 14, where in the plurality of beads range in size from about 10 µm to about 500 µm in diameter.

17. The device of claim 16, wherein the volume of the input cavity is at least about 2 to about 20 times the volume occupied by the plurality of beds.

18. A method for detecting a microbial contaminant in a liquid comprising:
    a) filtering a sample of a liquid through the device of claim 1, wherein microorganisms in the liquid are captured by the filter within the input cavity;
    b) sealing the output end of the device;
    c) dispensing into the input cavity an amount of a lysis solution sufficient to cover the filter;
    d) sealing the input end of the device;
    e) agitating the device, wherein agitating causes the at least one bead to strike the membrane, at least one captured microorganism, an inner surface of the device or a combination thereof, thereby forming a lysate of the captured microorganisms;
    f) recovering the lysate from the device; and
    g) detecting the presence or absence of a nucleic acid of at least one of the microorganisms in the recovered lysate, wherein the presence of the nucleic acid indicates a microbial contaminant in the liquid.

19. The method of claim 18, wherein the at least one bead is recovered with the lysate in step f), the method further comprising the step of agitating the recovered lysate and at the least one bead prior to detecting the nucleic acid.

20. The method of claim 18, further comprising incubating the device at a temperature between 50° C. and 90° C. after step c).

21. The method of claim 18, wherein the microorganisms are bacteria.

22. The method of claim 18, wherein the microorganisms are fungi.

23. The method of claim 18, wherein the microorganisms comprise a mixture of bacteria and fungi.

24. The method of claim 18, wherein detecting the nucleic acid consists of performing a PCR reaction with primers that amplify the nucleic acid.

25. The method of claim 24, wherein the lysis solution is a PCR-compatible lysis solution.

26. The method of claim 25, wherein the PCR-compatible lysis solution comprises at least one detergent selected from the group consisting of n-lauroyl sarcosine sodium, sodium deoxycholate, and Tween-20.

27. The method of claim 24, wherein the primers amplify a nucleic acid from a single species of bacteria or fungi.

28. The method of claim 24, wherein the primers comprises a pan-bacterial or pan-fungal primer pair.

29. The method of claim 24, wherein the PCR reaction is performed in the presence of a plurality primer pairs.

30. The method of claim 18, wherein the liquid is selected from the group consisting of water, a cell culture medium, a pharmacological solution and a biological solution.

31. A device for capture and lysis of microorganisms from a liquid comprising:
    a) a filter housing consisting of a hollow body defining a fluid path, having an upper input end adapted for receiving a liquid, a lower outflow end, and a filter cavity therebetween;
    b) a filter, having an input face and an output face, secured within the filter cavity in an orientation perpendicular to the fluid path wherein the filter is configured such that fluid can enter the input end of the housing and then pass through the filter before exiting the output end, wherein the filter divides the filter cavity into an upper input cavity between the input end of the housing and the input face of the filter, and a lower output cavity between the output face of the filter and the output end of the housing;

c) at least one bead disposed within the input cavity, wherein the bead can move freely within the input cavity when the device is agitated;

d) a first sealing means for removably sealing the input end, wherein the first sealing means is selected from a cap and a plug;

e) a second sealing means for removably sealing the output end, wherein the second sealing means is selected from a cap and a plug; and f) at least one ridge or baffle disposed on an inner surface of the input cavity.

\* \* \* \* \*